United States Patent

Schorr et al.

[11] 4,035,502
[45] July 12, 1977

[54] ACYLAMINOPENICILLANIC ACIDS AND PROCESS FOR PREPARING THEM

[75] Inventors: Manfred Schorr, Frankfurt am Main; Elmar Schrinner, Wiesbaden; Wilfried Schmitt, Kelkheim, Taunus, all of Germany

[73] Assignee: Hoechst Aktiengesellschaft, Frankfurt am Main, Germany

[21] Appl. No.: 637,116

[22] Filed: Dec. 3, 1975

[30] Foreign Application Priority Data

Dec. 5, 1974 Germany .......................... 2457464

[51] Int. Cl.² .............. C07D 499/76; A61K 31/43
[52] U.S. Cl. ............................ 424/271; 260/239.1
[58] Field of Search ................. 260/239.1; 424/271

[56] References Cited

U.S. PATENT DOCUMENTS 3,878,198   4/1975   Sircar et al. .................. 260/239.1
3,886,150   5/1975   Sellstedt et al. ............... 260/239.1

FOREIGN PATENT DOCUMENTS 1,260,882   1/1972   United Kingdom ........... 260/239.1

Primary Examiner—Gerald A. Schwartz
Attorney, Agent, or Firm—Curtis, Morris & Safford

[57] ABSTRACT

Acylaminopenicillanic acids of the general formula

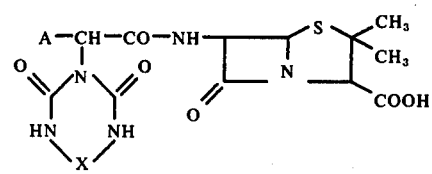

in which A represents phenyl which may be substituted, an aromatic monocyclic heterocycle which may be substituted or dihydrophenyl, and X represents one of the groups —SO₂—, —CO—, —P(R)— or —P(O)(-R)— in which R represents low molecular weight alkyl, alkenyl, alkoxy, aralkyl, aralkoxy, aryl or aryloxy which may be substituted, non-toxic salts of these compounds and pharmaceutical compositions containing these compounds.

12 Claims, No Drawings

ACYLAMINOPENICILLANIC ACIDS AND PROCESS FOR PREPARING THEM

The present invention provides derivatives of 6-aminopenicillanic acid of the general formula I

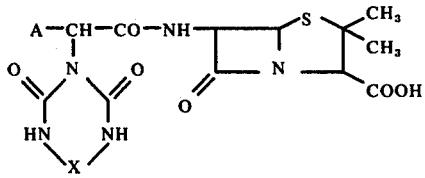

in which A represents phenyl which may be substituted, an aromatic monocyclic heterocycle which may be substituted or dihydrophenyl, and X represents one of the groups —$SO_2$—, —CO—, —P(R)— or —P(O)(R)—, in which R represents low molecular weight alkyl, alkenyl, alkoxy, aralkyl, aralkoxy, aryl or aryloxy which may be substituted, and non-toxic salts of these compounds.

The present invention furthermore relates to the preparation of these derivatives of the 6-aminopenicillanic acid and their salts, which process comprises a. reacting a diisocyanate of the general formula II

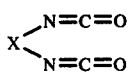

in which X has the meanings given above, with a compound of the general formula III

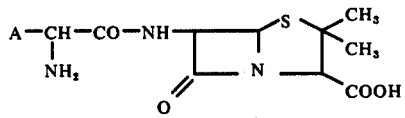

in which A has the meaning given above, or with a salt or an easily fissionable derivative of such a compound which is protected at the carboxyl group, or b. reacting an acid of the general formula IV

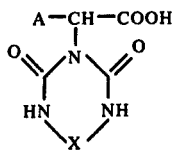

in which A and X have the meanings given above, or a reactive derivative of such an acid with 6-aminopenicillanic acid or with a salt or an easily fissionable derivative thereof which is protected at the carboxyl group, and, if desired or required, converting the esters obtained in this way to acids and/or, if desired or required, converting the acid into a salt or the salt into an acid.

Of the groups indicated for the symbol X, —$SO_2$— and —P(O)(R)— are preferred

R in the ring members —P(R)— and —P(O)(R)— represents a low molecular weight alkyl, alkenyl, or alkoxy radical. This radical may be a straight chain or branched radical of 1 to 5 carbon atoms, preferably a methyl, ethyl, vinyl, allyl, methoxy or ethoxy radical. These radicals may also be substituted, for example by alkoxy or alkyl-thioradicals of 1 to 4 carbon atoms, preferably by methoxy or methylthio groups.

If R represents aryl, aryloxy, aralkyl or aralkoxy alkyl and alkoxy having a chain length of 1 to 4 carbon atoms, there may be used, in particular, phenyl, phenoxy, benzyl or benzyloxy which may be substituted in the aryl radical, for example by lower alkyl, preferably methyl, chlorine, preferably halogen, or low molecular halogeno-alkyl, preferably trifluoromethyl.

Especially preferred R-groups are low molecular weight alkyl and low molecular weight alkoxy.

The preparation of the novel penicillin derivatives proceeds in a particularly simple manner by the reaction of a diisocyanato compound of the general formula II with penicillins of the general formula III which contain a free amino group in the molecule. Diisocyanates which are particularly suited for this reaction are, for example sulfonyl diisocyanate, carbonyl-diisocyanate, methyl-phosphinyl-diisocyanate, methyl-phosphino-diisocyanate, ethyl-phosphinyl-diisocyanate, n-propyl-phosphinyl-diisocyanate, isopropyl-phosphinyl-diisocyanate, butyl-phosphinyl-diisocyanate, iso-butyl-phosphinyl-diisocyanate, amylphosphinyl-diisocyanate, isoamyl-phosphinyl-diisocyanate, vinylphosphinyl-diisocyanate, allyl-phosphinyl-diisocyanate, benzyl-phosphinyl-diisocyanate, phenyl-ethyl-phosphinyl-diisocyanate, phenyl-phosphinyl-diisocyanate, 2-tolyl-phosphinyl-diisocyanate, 3-tolyl-phosphinyl-diisocyanate, 4-tolyl-phosphinyl-diisocyanate, 4-fluorophenyl-phosphinyl-diisocyanate, 4-chlorophenyl-phosphinyl-diisocyanate, 4-trifluoromethyl-phenyl-phosphinyl-diisocyanate, methoxy-phosphinyl-diisocyanate, ethoxy-phosphinyl-diisocyanate, propoxy-phosphinyl-diisocyanate, butoxy-phosphinyl-diisocyanate, benzyloxy-phosphinyl-diisocyanate and phenoxy-phosphinyl-diisocyanate.

The preparation of the sulfonyl-diisocyanate is described, for example in German Pat. No. 1,152,093 (1961) and German Pat. No. 1,171,887 (1961) and that of the carbonyl diisocyanate in Chem. Ber. 106, 1752 (1973). Methods for the preparation of the phosphinyl- and phosphino-diisocyanates are described, for example in J. Am. Chem. Soc. 78, 842 (1956); J. Org. Chem. 28, 586 (1963); Archiv der Pharmazie 301, 520 (1968); Zn. Obsch. Khim. 39, 1037 (1969); U.S. Pat. No. 3,177,239. The compounds of the formula III may be prepared, for example according to the method described in German Auslegeschrift No. 1,139,844.

A may represent, in particular, phenyl, but also substituted phenyl, the substituents being, for example hydroxyl, preferably methyl, alkoxy of 1 to 4 carbon atoms, preferably in the 4-position, alkyl of 1 to 4 carbon atoms, preferably methyl, alkoxy of 1 to 4 carbon atoms, preferably methoxy, or halogen, preferably chlorine or fluorine. Furthermore, A may represent dihydrophenyl or a monocyclic aromatic heterocycle, for example 2- or 3-thienyl, 2- or 3-furyl or 2-, 3- or 4-pyridyl, in which the heterocycles may also be substituted, for example by alkyl of 1 to 4 carbon atoms, preferably methyl, hydroxyl or alkoxy of 1 to 4 carbon atoms, preferably methoxy.

Particularly suitable penicillins of the general formula III are, for example 6-(α-amino-phenylacetylamino)-penicillanic acid, 6-(α-amino-4-hydroxyphenylacetylamino)-penicillanic acid, 6-(α-amino-2,5-dihydrophenylacetylamino)-penicillanic acid, 6-(α-amino-2-thienylacetylamino)-penicillanic acid 6-(α-amino-3-thienylacetylamino)-penicillanic acid, 6-(α-amino-3-thienylacetylamino)-penicillanic acid.

The reaction is advantageously carried out by adding a solution of the aminopenicillin of the formula III or of a salt thereof in an inert solvent to the diisocyanate of the formula II which may be dissolved in an inert solvent. As salts, there may be used, for example the alkali metal salts, in particular the sodium or potassium salts or, preferably, such amine salts which dissolve in the solvents used. Suitable solvents are, for example chlorinated hydrocarbons such as methylene chloride, chloroform of dimethylformamide. It is particularly advantageous to use a solution of the triethylamine salt in methylene chloride. The reaction is carried out at slightly reduced or normal temperatures, preferably between about −30° and +20° C. The treatment with a dilute mineral acid, for example hydrochloric or sulfuric acid, yields from the first formed salt the free acid of the penicillin of the invention which may then again be converted into other salts. It is often possible, however, to transform a first isolated amine salt directly into another salt, for example into an alkali metal salt. The reaction partners II and III are reacted in about equimolar amounts, but it may sometimes be advisable to use an excess of one or the other component.

Instead of the aminopenicillins of the general formula III, derivatives of these compounds may be used. For this purpose, esters may be used which may be split to the carboxylic acid in a neutral, acidic or weakly alkaline medium by solvolysis, for example by hydrolysis or alcoholysis, hydrogenolysis, reduction, nucleophilic exchange or photolysis.

Ester groups which can be easily split under neutral conditions by solvolysis with a solvent containing hydroxyl groups, for example, water or alcohols, are those which are derived from phosphinyl, silyl, germanyl, plumbyl or stannyl alcohols, for example, those described in DOS 2,222,094 (1974), in British Pat. No. 1,073,530, Netherland Patent Application No. 67/17107, laid open to public inspection, or DOS 1,800,690. Groups of the general formula $R_1R_2P(O)-O-CO-$ or $R_1R_2R_3Si-O-CO-$, in which $R_1$, $R_2$ and $R_3$ may be identical or different and represent, preferably, lower alkyl or aryl, for example phenyl, are preferred.

Esters which can be easily split in an acidic medium are those which are derived from lower alcohols, which are polybranched in the α-position or contain electron donors such as optionally substituted aromatic hydrocarbon radicals or heretocycles of aromatic nature which carry aroyl or acyloxy radicals. As examples, there may be mentioned the tert-butyl ester, the cyclohexyl ester, the adamantyl ester, the 2-tetrahydropyranyl ester, the p-nitrobenzyl ester, the benzhydryl ester, the trityl ester, the 3,4-dimethoxy-benzyl ester, the benzoyl-methyl ester, the acetoxy-methyl ester or the pivaloyloxy-methyl ester.

Ester groups which can be split off by hydrolysis in a weakly basic or acidic medium are, for example activated esters which are derived from optionally substituted phenol or benzyl alcohol, for example 4-nitrophenyl-, 2,4-dinitrophenyl-, 4-nitrobenzyl- or triphenylmethyl- ester.

The esters derived, for example from an optionally substituted benzyl alcohol, for example the 4-nitrobenzyl alcohol, may also be split by hydrogenolysis.

Ester groups which may be split reductively by treatment with nascent hydrogen or by electrolytic reduction are, for example ester groups which are derived from halogenated low molecular weight alcohols, for example 2,2,2-trichloroethanol, 2-chloroethanol, 2-bromoethanol or 4-pyridylmethanol.

Ester groups which can be split by photolysis, for example by ultra-violet light, are derived from aryl-substituted methanols in which the aryl groups may also be substituted. Such groups are, for example 4-methoxybenzyloxy-carbonyl, 3,5-dimethoxybenzyl-carbonyl or 2-nitrobenzyloxy-carbonyl.

The reaction of these derivatives of the aminopenicillins of the general formula III with the diisocyanate of the general formula II may also be effected in the manner described for the salts of the compounds of the formula III. It is followed by a splitting reaction carried out in known manner, for example by solvolysis, for example saponification by the action of water or diluted acids, or by a reductive splitting reaction, for example with catalytically excited hydrogen, or by a photolytic splitting reaction, for example by irradiation with ultra-violet light under neutral or acidic conditions.

The new penicillin derivatives of the general formula I may also be obtained by reacting acids of the general formula IV with 6-aminopenicillanic acid. This reaction can be carried out in known manner in the presence of a carbodiimide, such as dicyclohexyl-carbodiimide, as condensing agent. However, it is particularly advantageous to use the acids of the formula IV in the form of their reactive derivatives. As such, there may be used, for example the acid halides, preferably the acid chlorides, the acid azides, the acid anhydrides, mixed anhydrides, for example those with carbonic acid semi-esters, or low molecular weight fatty acids, for example pivalic acid, or the activated esters, for example the nitrophenyl- or dinitrophenyl-ester. The reaction proceeds particularly smoothly when working in the presence of solvents, for example water, low molecular weight ketones, in particular acetone or cyclic ethers such as tetrahydrofurane or dioxane, or mixtures of such solvents, and introducing the 6-aminopenicillanic acid in the form of a salt which is soluble in the solvent used. As salts, there may be used the same salts as those described for the compounds of the formula III. It is in this case also advantageous to use normal or slightly reduced temperatures, preferably temperatures in the range of from −50° to +20 ° C. The reaction components are preferably used in equivalent amounts, but the use of a respective excess is also possible. Isolation of the final products is effected in the manner already described.

The 6-aminopenicillanic acid may also be used in the form of easily splittable derivatives. Thus, especially those esters may be used which have been described above for the aminopenicillins of the formula III. If the esters are easily split by hydrolysis, the reaction with the acids of the general formula IV is carried out with the exclusion of water. Otherwise, the reaction may be carried out as described for the reaction of the compounds II and III.

The acids of the general formula IV, used as starting materials, can be obtained from the corresponding amino-acetic acids by the reaction with diisocyanates of the general formula II.

Conversion of the compounds of the formula I into salts, especially with physiologically tolerable bases, or the conversion of salts of compounds of the general formula I into the free acids is effected in known manner, for example by treatment of the carboxylic acid in solution with organic or inorganic bases or reaction of a salt with an acid.

As physiologically tolerable salts, there may be used in particular the alkali metal salts, preferably the disodium or potassium salts or salts with physiologically tolerable amines, for example triethylamine.

The new derivatives of the 6-aminopenicillanic acid of the general formula I generally are colorless crystalline compounds which, in the form of their amino salts or alkali metal salts, dissolve in water.

They have interesting antibiotic properties with a broad activity spectrum against bacterial pathogenic germs. This activity is particularly marked against gram-negative problematic germs, for example Pseudomonas or Proteus. By reason of these properties, the novel compounds are valuable therapeutics.

The compounds of the invention may be administered as such or in admixture with the therapeutically usual auxiliary agents, for example tragacanth, lactose, talc, solubilizers, etc., in the form of galenical compositions, for example tablets, dragees, capsules, or suspensions and solutions, which contain the active substance in an amount of about 50 to 1000 mg, preferably 100 to 500 mg. They may be administered perorally or parenterally. For parenteral administration, solutions of physiologically tolerated salts of the compounds of the formula I in a suitable solvent, for example water, are preferable.

It is also possible to combine the compounds of the invention with other active substances. Thus, for example, it is possible to administer simultaneously other antibiotics, for example those of the series of penicillins, cephalosporines or compounds which have an influence on the symptoms of bacterial infections, for example antipyretics, analgesics or antiphlogistics.

In addition to the acylaminopenicillanic acids described in the examples herein, there may also be obtained according to the invention, for example the compounds of the general formula

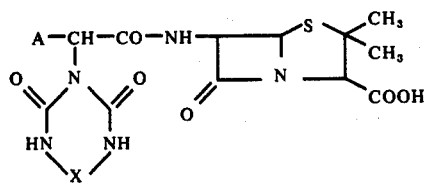

listed in the following table.

| A | X stands for $>P-R$ in which R represents |
|---|---|
| phenyl | methyl |
| phenyl | ethyl |
| phenyl | n-propyl |
| phenyl | i-propyl |
| phenyl | n-butyl |
| phenyl | i-butyl |
| phenyl | n-pentyl |
| phenyl | i-pentyl |
| phenyl | methoxy |
| phenyl | ethoxy |
| phenyl | propoxy |
| phenyl | butoxy |
| phenyl | vinyl |
| phenyl | allyl |
| phenyl | benzyl |
| phenyl | phenylethyl |
| phenyl | benzyloxy |
| phenyl | phenyl |
| phenyl | 2-tolyl |
| phenyl | 3-tolyl |
| phenyl | 4-tolyl |
| phenyl | 4-fluorophenyl |
| phenyl | 4-chlorophenyl |
| phenyl | 4-trifluoromethyl phenoxy |
| phenyl | methoxyethyl |
| phenyl | ethoxyethyl |
| phenyl | methylthioethyl |
| phenyl | 4-chlorobenzyl |
| phenyl | 4-trifluoromethylbenzyl |
| phenyl | 4-chlorobenzyloxy |
| phenyl | 4-trifluoromethylbenzyloxy |
| phenyl | 4-chlorophenoxy |
| 4-hydroxy-phenyl | methyl |
| 4-hydroxy-phenyl | ethyl |
| 4-hydroxy-phenyl | n-propyl |
| 4-hydroxy-phenyl | i-propyl |
| 4-hydroxy-phenyl | n-butyl |
| 4-hydroxy-phenyl | i-butyl |
| 4-hydroxy-phenyl | n-pentyl |
| 4-hydroxy-phenyl | i-pentyl |
| 4-hydroxy-phenyl | methoxy |
| 4-hydroxy-phenyl | ethoxy |
| 4-hydroxy-phenyl | propoxy |
| 4-hydroxy-phenyl | butoxy |
| 4-hydroxy-phenyl | vinyl |
| 4-hydroxy-phenyl | allyl |
| 4-hydroxy-phenyl | benzyl |
| 4-hydroxy-phenyl | phenylethyl |
| 4-hydroxy-phenyl | benzyloxy |
| 4-hydroxy-phenyl | phenyl |
| 4-hydroxy-phenyl | 2-tolyl |
| 4-hydroxy-phenyl | 3-tolyl |
| 4-hydroxy-phenyl | 4-tolyl |
| 4-hydroxy-phenyl | 4-fluorophenyl |
| 4-hydroxy-phenyl | 4-chlorophenyl |
| 4-hydroxy-phenyl | 4-trifluoromethyl phenoxy |
| 4-hydroxy-phenyl | methoxyethyl |
| 4-hydroxy-phenyl | ethoxyethyl |
| 4-hydroxy-phenyl | methylthioethyl |
| 4-hydroxy-phenyl | 4-chlorobenzyl |
| 4-hydroxy-phenyl | 4-trifluoromethylbenzyl |
| 4-hydroxy-phenyl | 4-chlorobenzyloxy |
| 4-hydroxy-phenyl | 4-trifluoromethylbenzyloxy |
| 4-hydroxy-phenyl | 4-chlorophenoxy |
| 2,5-dihydrophenyl | methyl |
| 2,5-dihydrophenyl | ethyl |
| 2,5-dihydrophenyl | n-propyl |
| 2,5-dihydrophenyl | i-propyl |
| 2,5-dihydrophenyl | n-butyl |
| 2,5-dihydrophenyl | i-butyl |
| 2,5-dihydrophenyl | n-pentyl |
| 2,5-dihydrophenyl | i-pentyl |
| 2,5-dihydrophenyl | methoxy |
| 2,5-dihydrophenyl | ethoxy |
| 2,5-dihydrophenyl | propoxy |
| 2,5-dihydrophenyl | butoxy |
| 2,5-dihydrophenyl | vinyl |
| 2,5-dihydrophenyl | allyl |
| 2,5-dihydrophenyl | benzyl |
| 2,5-dihydrophenyl | phenylethyl |
| 2,5-dihydrophenyl | benzyloxy |
| 2,5-dihydrophenyl | phenyl |
| 2,5-dihydrophenyl | 2-tolyl |
| 2,5-dihydrophenyl | 3-tolyl |
| 2,5-dihydrophenyl | 4-tolyl |
| 2,5-dihydrophenyl | 4-fluorophenyl |
| 2,5-dihydrophenyl | 4-chlorophenyl |
| 2,5-dihydrophenyl | 4-trifluoromethyl phenoxy |
| 2,5-dihydrophenyl | methoxyethyl |
| 2,5-dihydrophenyl | ethoxyethyl |
| 2,5-dihydrophenyl | methylthioethyl |
| 2,5-dihydrophenyl | 4-chlorobenzyl |
| 2,5-dihydrophenyl | 4-trifluoromethylbenzyl |
| 2,5-dihydrophenyl | 4-chlorobenzyloxy |
| 2,5-dihydrophenyl | 4-trifluoromethylbenzyloxy |
| 2,5-dihydrophenyl | 4-chlorophenoxy |
| 2-thienyl | methyl |

-continued

| A | X stands for $>\!\!\!\overset{\displaystyle O}{\underset{\displaystyle \|}{P}}\!\!-\!R$ in which R represents |
|---|---|
| 2-thienyl | ethyl |
| 2-thienyl | n-propyl |
| 2-thienyl | i-propyl |
| 2-thienyl | n-butyl |
| 2-thienyl | i-butyl |
| 2-thienyl | n-pentyl |
| 2-thienyl | i-pentyl |
| 2-thienyl | methoxy |
| 2-thienyl | ethoxy |
| 2-thienyl | propoxy |
| 2-thienyl | butoxy |
| 2-thienyl | vinyl |
| 2-thienyl | allyl |
| 2-thienyl | benzyl |
| 2-thienyl | phenylethyl |
| 2-thienyl | benzyloxy |
| 2-thienyl | phenyl |
| 2-thienyl | 2-tolyl |
| 2-thienyl | 3-tolyl |
| 2-thienyl | 4-tolyl |
| 2-thienyl | 4-fluorophenyl |
| 2-thienyl | 4-chlorophenyl |
| 2-thienyl | 4-trifluoromethyl |
| 2-thienyl | phenoxy |
| 2-thienyl | methoxyethyl |
| 2-thienyl | ethoxyethyl |
| 2-thienyl | methylthioethyl |
| 2-thienyl | 4-chlorobenzyl |
| 2-thienyl | 4-trifluoromethylbenzyl |
| 2-thienyl | 4-chlorobenzyloxy |
| 2-thienyl | 4-trifluoromethylbenzyloxy |
| 2-thienyl | 4-chlorophenoxy |
| 3-thienyl | methyl |
| 3-thienyl | ethyl |
| 3-thienyl | n-propyl |
| 3-thienyl | i-propyl |
| 3-thienyl | n-butyl |
| 3-thienyl | i-butyl |
| 3-thienyl | n-pentyl |
| 3-thienyl | i-pentyl |
| 3-thienyl | methoxy |
| 3-thienyl | ethoxy |
| 3-thienyl | propoxy |
| 3-thienyl | butoxy |
| 3-thienyl | vinyl |
| 3-thienyl | allyl |
| 3-thienyl | benzyl |
| 3-thienyl | phenylethyl |
| 3-thienyl | benzyloxy |
| 3-thienyl | phenyl |
| 3-thienyl | 2-tolyl |
| 3-thienyl | 3-tolyl |
| 3-thienyl | 4-tolyl |
| 3-thienyl | 4-fluorophenyl |
| 3-thienyl | 4-chlorophenyl |
| 3-thienyl | 4-trifluoromethyl |
| 3-thienyl | phenoxy |
| 3-thienyl | methoxyethyl |
| 3-thienyl | ethoxyethyl |
| 3-thienyl | methylthioethyl |
| 3-thienyl | 4-chlorobenzyl |
| 3-thienyl | 4-trifluoromethylbenzyl |
| 3-thienyl | 4-chlorobenzyloxy |
| 3-thienyl | 4-trifluoromethylbenzyloxy |
| 3-thienyl | 4-chlorophenoxy |
| phenyl | methyl |
| phenyl | ethyl |
| phenyl | n-propyl |
| phenyl | i-propyl |
| phenyl | n-butyl |
| phenyl | i-butyl |
| phenyl | n-pentyl |
| phenyl | i-pentyl |
| phenyl | methoxy |
| phenyl | ethoxy |
| phenyl | propoxy |
| phenyl | butoxy |
| phenyl | vinyl |
| phenyl | allyl |
| phenyl | benzyl |
| phenyl | phenylethyl |
| phenyl | benzyloxy |
| phenyl | phenyl |
| phenyl | 2-tolyl |
| phenyl | 3-tolyl |
| phenyl | 4-tolyl |
| phenyl | 4-fluorophenyl |
| phenyl | 4-chlorophenyl |
| phenyl | 4-trifluoromethyl |
| phenyl | phenoxy |
| phenyl | methoxyethyl |
| phenyl | ethoxyethyl |
| phenyl | methylthioethyl |
| phenyl | 4-chlorobenzyl |
| phenyl | 4-trifluoromethylbenzyl |
| phenyl | 4-chlorobenzyloxy |
| phenyl | 4-trifluoromethylbenzyloxy |
| phenyl | 4-chlorophenoxy |
| 4-hydroxy-phenyl | methyl |
| 4-hydroxy-phenyl | ethyl |
| 4-hydroxy-phenyl | n-propyl |
| 4-hydroxy-phenyl | i-propyl |
| 4-hydroxy-phenyl | n-butyl |
| 4-hydroxy-phenyl | i-butyl |
| 4-hydroxy-phenyl | n-pentyl |
| 4-hydroxy-phenyl | i-pentyl |
| 4-hydroxy-phenyl | methoxy |
| 4-hydroxy-phenyl | ethoxy |
| 4-hydroxy-phenyl | propoxy |
| 4-hydroxy-phenyl | butoxy |
| 4-hydroxy-phenyl | vinyl |
| 4-hydroxy-phenyl | allyl |
| 4-hydroxy-phenyl | benzyl |
| 4-hydroxy-phenyl | phenylethyl |
| 4-hydroxy-phenyl | benzyloxy |
| 4-hydroxy-phenyl | phenyl |
| 4-hydroxy-phenyl | 2-tolyl |
| 4-hydroxy-phenyl | 3-tolyl |
| 4-hydroxy-phenyl | 4-tolyl |
| 4-hydroxy-phenyl | 4-fluorophenyl |
| 4-hydroxy-phenyl | 4-chlorophenyl |
| 4-hydroxy-phenyl | 4-trifluoromethyl |
| 4-hydroxy-phenyl | phenoxy |
| 4-hydroxy-phenyl | methoxyethyl |
| 4-hydroxy-phenyl | ethoxyethyl |
| 4-hydroxy-phenyl | methylthioethyl |
| 4-hydroxy-phenyl | 4-chlorobenzyl |
| 4-hydroxy-phenyl | 4-trifluoromethylbenzyl |
| 4-hydroxy-phenyl | 4-chlorobenzyloxy |
| 4-hydroxy-phenyl | 4-trifluoromethylbenzyloxy |
| 4-hydroxy-phenyl | 4-chlorophenoxy |
| 2,5-dihydrophenyl | methyl |
| 2,5-dihydrophenyl | ethyl |
| 2,5-dihydrophenyl | n-propyl |
| 2,5-dihydrophenyl | i-propyl |
| 2,5-dihydrophenyl | n-butyl |
| 2,5-dihydrophenyl | i-butyl |
| 2,5-dihydrophenyl | n-pentyl |
| 2,5-dihydrophenyl | i-pentyl |
| 2,5-dihydrophenyl | methoxy |
| 2,5-dihydrophenyl | ethoxy |
| 2,5-dihydrophenyl | propoxy |
| 2,5-dihydrophenyl | butoxy |
| 2,5-dihydrophenyl | vinyl |
| 2,5-dihydrophenyl | allyl |
| 2,5-dihydrophenyl | benzyl |
| 2,5-dihydrophenyl | phenylethyl |
| 2,5-dihydrophenyl | benzyloxy |
| 2,5-dihydrophenyl | phenyl |
| 2,5-dihydrophenyl | 2-tolyl |
| 2,5-dihydrophenyl | 3-tolyl |
| 2,5-dihydrophenyl | 4-tolyl |
| 2,5-dihydrophenyl | 4-fluorophenyl |
| 2,5-dihydrophenyl | 4-chlorophenyl |
| 2,5-dihydrophenyl | 4-trifluoromethyl |
| 2,5-dihydrophenyl | phenoxy |
| 2,5-dihydrophenyl | methoxyethyl |
| 2,5-dihydrophenyl | ethoxyethyl |
| 2,5-dihydrophenyl | methylthioethyl |
| 2,5-dihydrophenyl | 4-chlorobenzyl |
| 2,5-dihydrophenyl | 4-trifluoromethylbenzyl |
| 2,5-dihydrophenyl | 4-chlorobenzyloxy |
| 2,5-dihydrophenyl | 4-trifluoromethylbenzyloxy |
| 2,5-dihydrophenyl | 4-chlorophenoxy |
| 2-thienyl | methyl |
| 2-thienyl | ethyl |
| 2-thienyl | n-propyl |
| 2-thienyl | i-propyl |
| 2-thienyl | n-butyl |
| 2-thienyl | i-butyl |
| 2-thienyl | n-pentyl |

-continued

| A | in which R represents |
|---|---|
| 2-thienyl | i-pentyl |
| 2-thienyl | methoxy |
| 2-thienyl | ethoxy |
| 2-thienyl | propoxy |
| 2-thienyl | butoxy |
| 2-thienyl | vinyl |
| 2-thienyl | allyl |
| 2-thienyl | benzyl |
| 2-thienyl | phenylethyl |
| 2-thienyl | benzyloxy |
| 2-thienyl | phenyl |
| 2-thienyl | 2-tolyl |
| 2-thienyl | 3-tolyl |
| 2-thienyl | 4-tolyl |
| 2-thienyl | 4-fluorophenyl |
| 2-thienyl | 4-chlorophenyl |
| 2-thienyl | 4-trifluoromethyl |
| 2-thienyl | phenoxy |
| 2-thienyl | methoxyethyl |
| 2-thienyl | ethoxyethyl |
| 2-thienyl | methylthioethyl |
| 2-thienyl | 4-chlorobenzyl |
| 2-thienyl | 4-trifluoromethyl |
| 2-thienyl | 4-chlorobenzyloxy |
| 2-thienyl | 4-trifluoromethylbenzyloxy |
| 2-thienyl | 4-chlorophenoxy |
| 3-thienyl | methyl |
| 3-thienyl | ethyl |
| 3-thienyl | n-propyl |
| 3-thienyl | i-propyl |
| 3-thienyl | n-butyl |
| 3-thienyl | i-butyl |
| 3-thienyl | n-pentyl |
| 3-thienyl | i-pentyl |
| 3-thienyl | methoxy |
| 3-thienyl | ethoxy |
| 3-thienyl | propoxy |
| 3-thienyl | butoxy |
| 3-thienyl | vinyl |
| 3-thienyl | allyl |
| 3-thienyl | benzyl |
| 3-thienyl | phenylethyl |
| 3-thienyl | benzyloxy |
| 3-thienyl | phenyl |
| 3-thienyl | 2-tolyl |
| 3-thienyl | 3-tolyl |
| 3-thienyl | 4-tolyl |
| 3-thienyl | 4-fluorophenyl |
| 3-thienyl | 4-chlorophenyl |
| 3-thienyl | 4-trifluoromethyl |
| 3-thienyl | phenoxy |
| 3-thienyl | methoxyethyl |
| 3-thienyl | ethoxyethyl |
| 3-thienyl | methylthioethyl |
| 3-thienyl | 4-chlorobenzyl |
| 3-thienyl | 4-trifluoromethylbenzyl |
| 3-thienyl | 4-chlorobenzyloxy |
| 3-thienyl | 4-trifluoromethylbenzyloxy |
| 3-thienyl | 4-chlorophenoxy |

The following Examples illustrate the invention:

EXAMPLE 1

6-[D-α-(1,1-Dioxido-3,5-dioxo-1,2,4,6-thiatriazine-4-yl)-phenylacetylamino]-penicillanic acid A solution of 3.5 g of 6-(D-α-amino-phenylacetylamino)-penicillanic acid and 1.53 g of triethylamine in 60 ml of anhydrous methylene chloride was added dropwise to a solution of 1.48 g of sulfonyl-diisocyanate in 60 ml of anhydrous methylene chloride which solution had been cooled to −10° C. The reaction solution was stirred for 1 hour at 0° C and then evaporated under reduced pressure. The foamy residue was triturated with ether and filtered off with suction. The yield of crude product was 6 g. This triethyl-ammonium salt was dissolved in 10 ml of water and combined with 10 ml of 2N hydrochloric acid. The 6[D-α-(1,1-dioxido-3,5-dioxo-1,2,4,6-thiatriazine-4-yl)-phenylacetylamino]-penicillanic acid crystallized immediately. The colorless crystals were filtered off with suction and washed with water. After drying under reduced pressure, 4.2 g of substance were obtained. The substance was found to decompose at 155° C.

The infrared spectrum and NMR spectrum corresponded with the indicated structure.

The compound was found to dissolve easily in dilute sodium bicarbonate solution.

EXAMPLE 2

6-[D-α-(1-ethyl-1-oxido-3,5-dioxo-hexahydro-1,2,4,6-phosphatriazine-4-yl)-phenylacetylamino]-penicillanic acid 7 g of 6-(D-α-amino-phenylacetylamino)-penicillanic acid and 3.3g of triethylamine were dissolved in 120 ml of anhydrous methylene chloride and added dropwise, while stirring, at −15° C, to a solution of 3.2 g of ethyl-phosphinyl-diisocyanate in 120 ml of anhydrous methylene chloride. The reaction solution was then stirred for 30 minutes at −10° C and for 1 hour at room temperature. After evaporation of the solvent under reduced pressure, the amorphous residue was dissolved in 100 ml of water and the whole was adjusted to a pH-value of 2 by means of 1N-aqueous hydrochloric acid. The product which had crystallized was filtered off with suction and washed with water. After drying under reduced pressure, 6.2 g of 6-(D-α-(1-ethyl-1-oxido-3,5-dioxohexahydro-1,2,4,6-phosphatriazine-4-yl)-phenylacetylamino]-penicillanic acid having a decomposition point of 163° C were obtained.

The infrared spectrum and NMR spectrum corresponded to the indicated structure.

The sodium salt was obtained by solution of the acid in an aqueous sodium bicarbonate solution and subsequent lyophilization.

EXAMPLE 3

6-[D-α-(1,1-Dioxido-3,5-dioxo-1,2,4,6-thiatriazine-4-yl)-phenylacetylamino]-penicillanic acid A solution of 2.2 g of trimethyl-chlorosilane in 10 ml of anhydrous methylene chloride was added dropwise to a solution, cooled to 0° C, of 3.5 g of 6-(D-α-amino-phenylacetylamino)- penicillanic acid and 2.02 g of triethylamine in 60 ml of anhydrous methylene chloride. The reaction solution was stirred for 1 hour at 0° C and then added dropwise, at −10°, C to a solution of 1.48 g of sulfonyl-diisocyanate in 60 ml of anhydrous methylene chloride. The reaction mixture was stirred for 1 hour at 0° C and then evaporated under reduced pressure. The amorphous residue was combined with 50 ml of water and 5 ml of 2N-hydrochloric acid. The 6-(D-α-(1,1-dioxido-3,5-dioxo-1,2,4,6-thiatriazine-4-yl)-phenylacetylamino]-penicillanic acid crystallized in the form of colorless crystals. The product was filtered off with suction, washed with water and dried under reduced pressure. 3.4 g of substance were obtained having a decomposition point of 155° C.

We claim:
1. An acylaminopenicillanic acid of the formula

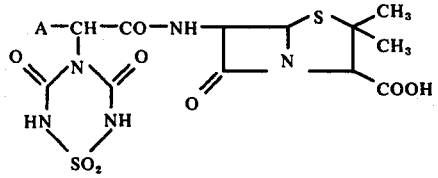

wherein A is phenyl; hydroxyphenyl; alkylphenyl, said alkyl being of from 1 to 4 carbon atoms; alkoxyphenyl, said alkoxy being of from 1 to 4 carbon atoms; halophenyl; dihydrophenyl; a conventional aromatic monocyclic heterocycle attached to the —CH of the acetyl group of a 6-acetylamino moiety attached to a penicillin ring; or said aromatic monocyclic heterocycle substituted by alkyl of from 1 to 4 carbon atoms, hydroxyl, or alkoxy of from 1 to 4 carbon atoms; or a non-toxic salt thereof.

2. A non-toxic salt of an acylaminopenicillanic acid as defined in claim 1, which is an alkali salt or a salt with a physiologically tolerable amine.

3. An acylaminopenicillanic acid as defined in claim 1, wherein said aromatic monocyclic heterocycle is thienyl, furyl or pyridyl; or a non-toxic salt thereof.

4. An acylaminopenicillanic acid as defined in claim 3, wherein said thienyl is 2-thienyl; or 3-thienyl said furyl is 2-furyl or 3-furyl; and said pyridyl is 2-pyridyl, 3-pyridyl or 4-pyridyl; or a non-toxic salt thereof.

5. An acylaminopenicillanic acid as defined in claim 1, wherein said alkyl is methyl, said alkoxy is methoxy and said halophenyl is chlorophenyl or fluorophenyl; or a non-toxic salt thereof.

6. A composition active against bacterial infections, which comprises an antibacterial effective amount of an acylaminopenicillanic acid of the formula

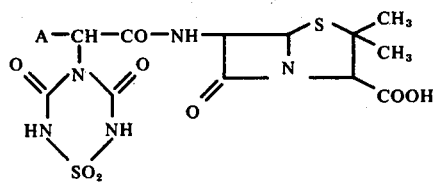

wherein A is phenyl; hydroxyphenl; alkylphenyl, said alkyl being of from 1 to 4 carbon atoms; alkoxyphenyl, said alkoxy being of from 1 to 4 carbon atoms; halophenyl; dihydrophenyl; a conventional aromatic monocyclic heterocycle attached to the —CH of the acetyl group of a 6-acetylamino moiety attached to a penicillin ring; or said aromatic monocyclic heterocycle substituted by alkyl of from 1 to 4 carbon atoms, hydroxyl, or alkoxy of from 1 to 4 carbon atoms; and a customary therapeutic auxiliary agent.

7. The composition as defined in claim 6, wherein the auxiliary agent is tragacanth, lactose, talc or a solubilizer.

8. The composition as defined in claim 6, wherein said aromatic monocyclic heterocylce is thienyl, furyl or pyridyl.

9. The composition as defined in claim 8 wherein said thienyl is 2-thienyl or 3 -thienyl; said furyl is 2-furyl or 3-furyl; and said pyridyl is 2-pyridyl, 3-pyridyl or 4-pyridyl.

10. The composition as defined in claim 8, wherein the auxiliary agent is tragacanth, lactose, talc or a solubilizer.

11. A method of treatment against bacterial infection which comprises administering to an organism having such infection an antibacterial effective amount of a compound defined in claim 1.

12. 6[D-α-(1,1-Dioxido-3,5-dioxo-1,2,4,6-thiatriazine-4-yl)-phenylacetylamino]-penicillanic acid.

* * * * *